(12) United States Patent
Xing et al.

(10) Patent No.: US 12,102,956 B2
(45) Date of Patent: Oct. 1, 2024

(54) METHOD FOR THE ADSORPTIVE SEPARATION OF ETHYLENE AND ETHANE USING ULTRAMICROPOROUS METAL-ORGANIC FRAMEWORK

(71) Applicant: ZHEJIANG UNIVERSITY, Hangzhou (CN)

(72) Inventors: Huabin Xing, Hangzhou (CN); Qi Ding, Hangzhou (CN); Xili Cui, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 534 days.

(21) Appl. No.: 17/426,587

(22) PCT Filed: Jan. 22, 2020

(86) PCT No.: PCT/CN2020/073776
§ 371 (c)(1),
(2) Date: Jul. 28, 2021

(87) PCT Pub. No.: WO2020/156426
PCT Pub. Date: Aug. 6, 2020

(65) Prior Publication Data
US 2022/0096992 A1 Mar. 31, 2022

(30) Foreign Application Priority Data
Jan. 29, 2019 (CN) .......................... 201910084873.8

(51) Int. Cl.
*B01D 53/02* (2006.01)
*B01J 20/22* (2006.01)
(Continued)

(52) U.S. Cl.
CPC .............. *B01D 53/02* (2013.01); *B01J 20/22* (2013.01); *B01J 20/28* (2013.01); *C07C 7/12* (2013.01); *B01D 2253/204* (2013.01)

(58) Field of Classification Search
None
See application file for complete search history.

(56) References Cited

U.S. PATENT DOCUMENTS

2016/0159713 A1  6/2016 Long et al.
2019/0054446 A1* 2/2019 Long .................... B01J 20/3491

FOREIGN PATENT DOCUMENTS

CN  105037403  11/2015
CN  108329484  7/2018
(Continued)

OTHER PUBLICATIONS

P. Bereciartua, et al., Control of Zeolite Framework Flexibility & Pore Topology for Separation of Ethane and Ethylene, Science 358, 1068-1071 (2017).

*Primary Examiner* — Gabriel E Gitman
(74) *Attorney, Agent, or Firm* — Jiwen Chen; Joywin IP Law PLLC

(57) ABSTRACT

The present invention provides a method for the adsorptive separation of $C_2H_4$ and $C_2H_6$ using ultramicroporous metal-organic framework material, comprising the following steps that (1) $C_2H_4/C_2H_6$ mixture is contacted with the ultramicroporous metal-organic framework material; (2) $C_2H_4$ is preferentially adsorbed and the separation of $C_2H_4/C_2H_6$ is realized. The described "ultramicroporous metal-organic framework material" has a formula of $[M_3L_3A]_\infty$, wherein M represents the metal cation being any one of $Cu^{2+}$, $Zn^{2+}$, $Co^{2+}$, and $Ni^{2+}$; L represents the organic linker being any one of 1,2,4-triazole and its derivatives; A represents the oxygen-containing inorganic anion being any one of $PO_4^{3-}$ and $VO_4^{3-}$. The class of ultramicroporous metal-organic (Continued)

frameworks has optimal pore size and pore chemistry, exhibiting both higher uptake capacity and faster adsorption rate for $C_2H_4$ as compared to $C_2H_6$, thus $C_2H_4$ can be preferentially adsorbed by these metal-organic frameworks with high selectivity, and high-purity $C_2H_4$ can be separated from $C_2H_4/C_2H_6$ mixtures efficiently.

10 Claims, 5 Drawing Sheets

(51) Int. Cl.
    *B01J 20/28*     (2006.01)
    *C07C 7/12*     (2006.01)

(56) References Cited

FOREIGN PATENT DOCUMENTS

| | | |
|---|---|---|
| CN | 108579686 | 9/2018 |
| WO | WO2016162834 A8 | 12/2016 |

* cited by examiner

METHOD FOR THE ADSORPTIVE SEPARATION OF ETHYLENE AND ETHANE USING ULTRAMICROPOROUS METAL-ORGANIC FRAMEWORK

This is a U.S. national stage application of PCT Application No. PCT/CN2020/073776 under 35 U.S.C. 371, filed Jan. 22, 2020 in Chinese, claiming priority of Chinese Application No. 201910084873.8, filed Jan. 29, 2019, all of which are hereby incorporated by reference.

TECHNOLOGY FIELD

The present invention relates to the field of chemical separation engineering, and in particular relates to a method for the adsorptive separation of ethylene/ethane ($C_2H_4$/$C_2H_6$) mixtures using ultramicroporous metal-organic framework.

BACKGROUND TECHNOLOGY

As one of the largest chemicals in term of production capacity, ethylene ($C_2H_4$) is the core of petrochemical industries, and an important indicator of the development level of a country's petrochemical industry. The downstream derivatives of $C_2H_4$ mainly include polyethylene, polyvinyl chloride, ethylene oxide, ethylene glycol, vinyl acetate, etc., which account for more than 75% of the petrochemicals and are widely utilized in the manufacture of synthetic plastics, pharmaceuticals, textiles and coating materials. At present, the industry mainly uses naphtha as a raw material, cracking it into a variety of low-carbon hydrocarbon mixtures and then separating and extracting ethylene from it. Attributed to the highly similar physiochemical properties and molecular size of $C_2H_4$ and $C_2H_6$, their separation represents a critical step in the production of high-purity $C_2H_4$, which, however, still remains a great challenge.

Cryogenic distillation has long been the most widely applied technique for $C_2H_4$/$C_2H_6$ separation in industry. However, this technology has high requirements on operating conditions and equipment. Due to the low relative volatility between $C_2H_4$ and $C_2H_6$, the separation process has to be conducted under extremely high pressure (22 bar), extremely low temperature (−160° C.) and large reflux ratio, and the number of plates/trays in distillation tower usually exceeds 100. The low-temperature rectification method has high energy consumption, complex process flow, and large investment in equipment. Therefore, it is urgent to develop new alternative technologies.

Adsorptive separation is an emerging energy-saving gas separation technique, which can enable effective gas separation and purification under mild conditions. With the glaring merits of high energy efficiency, facile manipulation, and easy scaling-up, adsorptive separation has shown great promise for the separation of various industrially important gases, including $C_2H_4$/$C_2H_6$ gas mixtures. Notably, to develop novel adsorbents that simultaneously present high gas uptake capacity, excellent separation selectivity, and desirable stability is an important start point to realize the highly efficient adsorptive separation. However, in the aspect of $C_2H_4$/$C_2H_6$ separation, it still remains an intractable issue to design such high-performance porous materials that can fulfill all these demands, especially the trade-off between gas uptake and separation selectivity is hard to break. For instance, Avelino Corma and co-workers recently reported a flexible pure silica zeolite ITQ-55 that exhibits quite high kinetic selectivity for $C_2H_4$ over $C_2H_6$, but the $C_2H_4$ uptake on this material is low, only 1.5 mmol g$^{-1}$ under 303 K (30° C.) and 1 bar (Control of zeolite framework flexibility and pore topology for separation of ethane and ethylene, Science, 2017, 358, 1068-1071). According to the report from Zongbi Bao et al, Mg-MOF-74 can preferentially trap $C_2H_4$ with a high uptake capacity of 7.5 mmol g$^{-1}$ under 298 K and 1 bar, whereas its separation selectivity is less than 10 for equimolar $C_2H_4$/$C_2H_6$ mixture (Adsorption of Ethane, Ethylene, Propane, and Propylene on a Magnesium-Based Metal-Organic Framework, Langmuir, 2011, 27, 13554-13562). Transition metal ion-based adsorbents such as molecular sieve AgA (Journal of the American Chemical Society, 2012, 134(36): 14635-14637.), organic porous material PAF-1-SO$_3$Ag (Journal of the American Chemical Society, 2014, 136 (24): 8654-8660.), CuCl-supported alumina (CN 1048010C), etc. also can be used for $C_2H_4$/$C_2H_6$ separation attributed to their strong π-complexation interactions with $C_2H_4$. However, these materials are susceptible to contamination by moisture and sulfur compounds in the feed gas, and exhibit poor stability performance short service life, and high regeneration energy consumption, which is not suitable for industrial applications. Therefore, it is urgent to develop new ethylene/ethane selective adsorption materials and effective adsorption separation methods.

SUMMARY OF THE INVENTION

The present invention provides a method for the separation of $C_2H_4$ and $C_2H_6$ which can achieve separation of $C_2H_4$ and $C_2H_6$ in a highly efficient manner.

A method for adsorbing and separating ethylene and ethane based on an ultra-microporous metal-organic framework material includes the following steps: contacting a mixed gas of ethylene and ethane with an ultra-microporous metal-organic framework material to adsorb ethylene in the mixed gas to achieve separation of ethane and ethylene.

The chemical formula of the ultra-microporous metal organic framework material is [M$_3$L$_3$A]$_\infty$, where M is a metal cation, L is an organic linker or ligand and A is an oxygen-containing inorganic ion and the material is constructed by metal cation M, organic linker L and oxygen-containing inorganic anion A.

The organic linker is 1,2,4-triazole and its derivatives, and the structural formula is

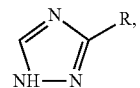

wherein R is one of H, CH$_3$, NH$_2$, SH, F, Cl, and Br;
the metal cation is one of Cu$^{2+}$, Zn$^{2+}$, Co$^{2+}$, and Ni$^{2+}$;
the oxygen-containing inorganic anion is PO$_4^{3-}$ or VO$_4^{3-}$.

The present invention realizes the precise control of the pore diameter of the ultra-microporous metal organic framework material through the combination of different anions, cations and organic linkers. When the mixed gas containing ethylene and ethane contacts the ultra-microporous metal organic framework material, due to the reason that ethylene/ethane molecules' difference in size causes a significant difference in the diffusion rate of the two in the material pores, ethylene travels faster than ethane. At the same time, due to the high density of oxygen-containing anions distributed on the surface of the pores, the material exhibits stronger host-guest interactions towards ethylene molecules with higher hydrogen bond acidity, resulting in ethylene having a higher adsorption capacity than ethane, which further enhances the ability of molecular recognition of the metal organic framework material, so as to obtain high-purity ethylene gas and ethane gas.

In the present invention, the ultra-microporous metal-organic framework material composed of the oxygen-containing inorganic anion A, the metal cation M and the organic linker L has the specific structure shown in FIGS. 9a and b from different angles, in which,

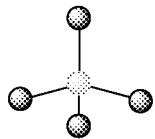

is oxygen-containing inorganic anion,

is a metal cation and

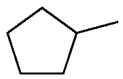

is 1,2,4-triazole and its derivatives.

In the ultra-microporous metal-organic framework material structure, the organic linkers are coordinated with the metal cations through the nitrogen atoms on the triazole ring to form a positively charged two-dimensional layered structure, in which some of the organic linkers bind to two metal cations at the same time in a two-coordination manner, and some organic linkers combine with three metal cations at the same time in a three-coordination manner; oxygen-containing anions are connected to metal cations located in different layers through oxygen atoms to form a one-dimensional channel structure decorated by high-density electronegative oxygen atoms. In the extension direction of the pores, the two-coordinated organic linkers are arranged antiparallelly, so that the pore size changes periodically. The narrowest part of the pore size is 3.0~4.2 Å, which specifically refers to the distance between the R groups of the closest organic linker on both sides of the pore.

The ultramicroporous metal-organic framework can be synthesized by hydrothermal method, in which inorganic salts or inorganic acids containing metal cations and oxygen-containing inorganic anions react with organic linkers/ligands under alkaline conditions (7.0<pH<10.0) and, using a mixed solvent of water and alcohols (such as methanol). The molar ratio of organic linker/ligand to metal cation and organic ligand to oxygen-containing inorganic anion in the initial reaction system are both 1:1~50:1, and the reaction temperature is 65~210° C.

Preferably, the inorganic oxygen-containing anion is $PO_4^{3-}$, the metal cation is $Zn^{2+}$, and the organic linker is 3-methyl-1,2,4-triazole. The resultant ultramicroporous metal-organic framework material is Zn-Ctz-$PO_4$. The equilibrium adsorption capacity of the ultra-microporous Zn-Ctz-$PO_4$ for ethylene and ethane at 1 bar and 298 K is 1.5 mmol $g^{-1}$ and 0.5 mmol $g^{-1}$, respectively, and the thermodynamic-kinetic combined selectivity is 15.

Still preferably, the inorganic oxygen-containing anion is $PO_4^{3-}$, the metal cation is $Zn^{2+}$, and the organic linker is 3-amino-1,2,4-triazole. The resultant ultramicroporous metal-organic framework material is Zn-Atz-$PO_4$. The equilibrium adsorption capacity of the ultra-microporous Zn-Atz-$PO_4$ for ethylene and ethane at 1 bar and 273 K is 2.4 mmol $g^{-1}$ and 0.9 mmol $g^{-1}$, respectively, and the kinetic selectivity is 27, and the combined selectivity is about 20.

Preferably, the volume ratio of ethylene to ethane in the mixed gas of ethylene and ethane is 1:99 to 99:1.

The volume ratio of ethylene and ethane components in the mixed gas is 1:99 to 99:1 (such as 50:50, 90:10), and the mixed gas may contain impurity components such as hydrogen, nitrogen, oxygen, sulfur compounds (such as sulfur dioxide), nitrogen oxides (such as nitrogen monoxide, nitrogen dioxide, etc.), carbon oxides (such as carbon monoxide, carbon dioxide), water moisture and other low-carbon hydrocarbons (such as methane, propylene, propane, etc.) without affecting the separation performance of the ultra-microporous metal organic framework materials for ethylene/ethane components.

The ultra-microporous metal organic frame material can separate ethane gas with a purity of more than 99% and ethylene gas with a purity of 95-99% from the mixed gas containing ethylene and ethane, and the ethylene recovery rate is not less than 70%.

The operation mode of the separation method of the present invention is any one of fixed bed adsorption, fluidized bed adsorption, and moving bed adsorption.

This kind of crystalline material has one-dimensional pore channels with a periodically expanded and contracted cross-section, meanwhile the pore surface is decorated by high-density electronegative anion pillars. By changing the kinds of metal cations, inorganic anions and organic linkers, the pore size can be precisely tuned in the range of 3.0~4.2 Å, which matches well with the kinetic diameter of $C_2H_4$ (4.16 Å) but is clearly smaller than that of $C_2H_6$ (4.44 Å). Attributed to the optimal pore size and pore chemistry of the metal-organic framework, $C_2H_4$ can diffuse more rapidly in the pore channel meanwhile interact more strongly with the anion pillars through hydrogen bonding interactions.

Preferably, the method is implemented by fixed-bed adsorptive separation, which comprises the following steps:

(1) under a pre-determined temperature and pressure, a flow of $C_2H_4/C_2H_6$ mixture is introduced into a fixed-bed sorption column packed with the ultramicroporous metal-organic framework, which allows $C_2H_4$ to diffuse more rapidly in the pore channel and interact more strongly with the pore surface as compared to $C_2H_6$, so that $C_2H_4$ can be retained in the column for a long time while $C_2H_6$ can penetrate the column quickly, allowing high-purity $C_2H_6$ to be immediately produced before the breakthrough of $C_2H_4$;

(2) after $C_2H_4$ breaks through, the flow of $C_2H_4/C_2H_6$ mixture is turned off, then the $C_2H_4$ component adsorbed by the metal-organic framework is released by means of pressure reduction, temperature increasing, inert gas purge, and pure gas purge, or any combination of them, so that high-purity $C_2H_4$ can be obtained.

During the separation process, the temperature for adsorption is in the range of −50~100° C. Under a relatively lower temperature, the uptake capacity of $C_2H_4$ on the ultramicroporous metal-organic framework can be higher, and the diffusion of $C_2H_6$ can be slower, leading to a higher separation selectivity. Under a relatively higher temperature, the desorption of $C_2H_4$ can be more facilely manipulated with less energy consumption. Preferably, the temperature for adsorption is in the range of –10~25° C.

The adsorption of the gas mixture on the ultramicroporous metal-organic framework is carried out under a pressure of 0~10 bar. Preferably, the pressure for the adsorption is in the range of 1~5 bar.

The desorption of the gas is carried out under a temperature of 25~150° C. and preferably, the temperature for the desorption is in the range of 65–100° C.

The desorption pressure is 0 to 1 bar, preferably 0~0.2 bar.

Compared to the prior art methods, the outstanding advantages of the present inventions are as follows:

(1) The present invention offers a novel method for the effective adsorptive separation of $C_2H_4$ and $C_2H_6$ using ultramicroporous metal-organic framework. The metal-organic framework exhibits a higher equilibrium uptake capacity for $C_2H_4$ over $C_2H_6$, meanwhile its adsorption rate for $C_2H_4$ is also significantly faster than that for $C_2H_6$. Through the synergetic effect of equilibrium and adsorption kinetics, highly efficient $C_2H_4$/$C_2H_6$ separation can be realized by the ultramicroporous metal-organic framework, and high-purity $C_2H_4$ can be easily obtained from $C_2H_4$/$C_2H_6$ mixtures.

(2) Compared to the conventional adsorbents utilized for $C_2H_4$/$C_2H_6$ separation, the metal-organic framework presented in this invention well combines excellent equilibrium and kinetic selectivities towards $C_2H_4$. The overall separation selectivity and $C_2H_4$ uptake capacity of the metal-organic framework are both remarkably superior to other adsorbents based on only single separation mechanism (either equilibrium or kinetic separation mechanism).

(3) The metal-organic framework presented in this invention can be facilely synthesized from cheap reagents, and also can be easily regenerated for repeated use in a long lifetime. Especially, the metal-organic framework shows excellent stability under high-temperature and humid conditions. Its thermal decomposition temperature can be up to 400° C., and the crystalline structure can be well retained even after exposed to air (25° C., relative humidity 70%) for 60 days or soaked in water for 48 hours. These merits indicate the ultra-microporous metal-organic framework presented in this invention has a good prospect for industrial application.

(4) By the method provided by this invention, the highest purities of $C_2H_4$ and $C_2H_6$ separated from their mixtures can be 99.0% and 99.999%, respectively.

(5) Compared to the conventional thermal-driven cryogenic distillation technique, the method provided by the present invention can be facilely conducted under mild operation conditions accompanied by much lower energy consumption and capital cost. Consequently, the method presented in this invention has great potential for commercial-scale $C_2H_4$/$C_2H_6$ separation and is expected to create more economic benefits and business value.

SPECIFIC EMBODIMENTS OF THE INVENTION

Example 1

Figure 1:
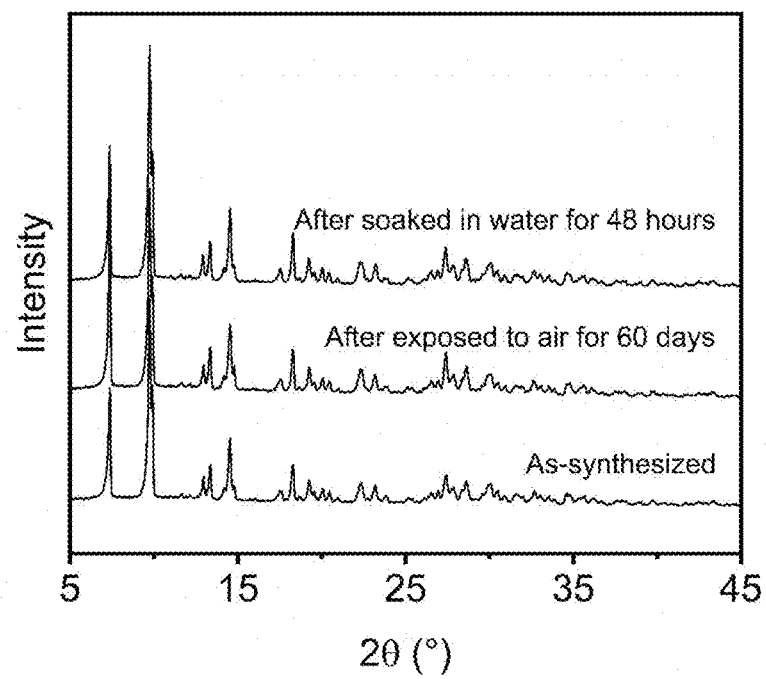
FIG. 1 shows the powder X-ray diffraction pattern of the ultramicroporous metal-organic framework Zn-Atz-$PO_4$ synthesized in exampled 1.
Figure 2:
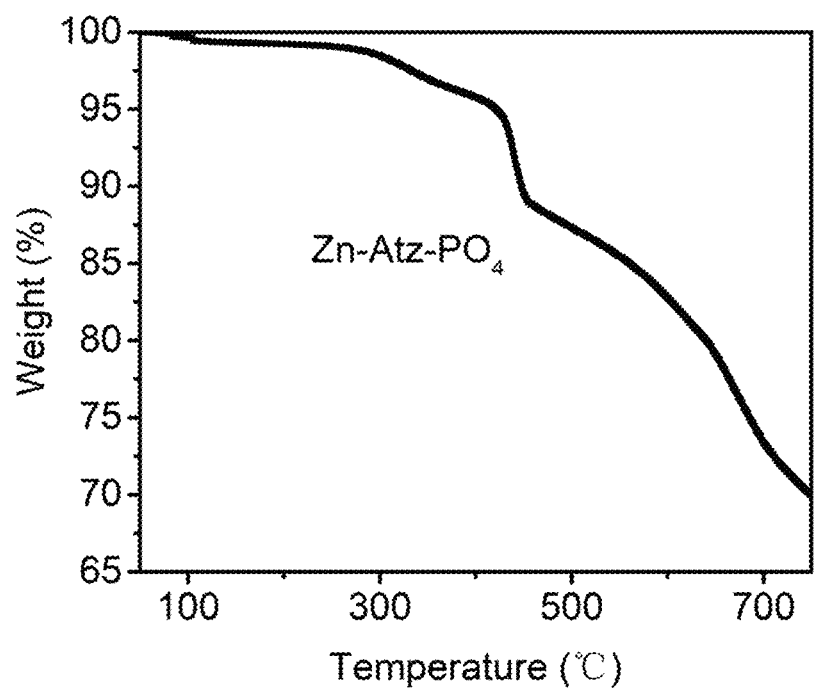
FIG. 2 shows the thermal gravimetric analysis curve of the ultramicroporous metal-organic framework Zn-Atz-$PO_4$ synthesized in exampled 1.
Figure 3:
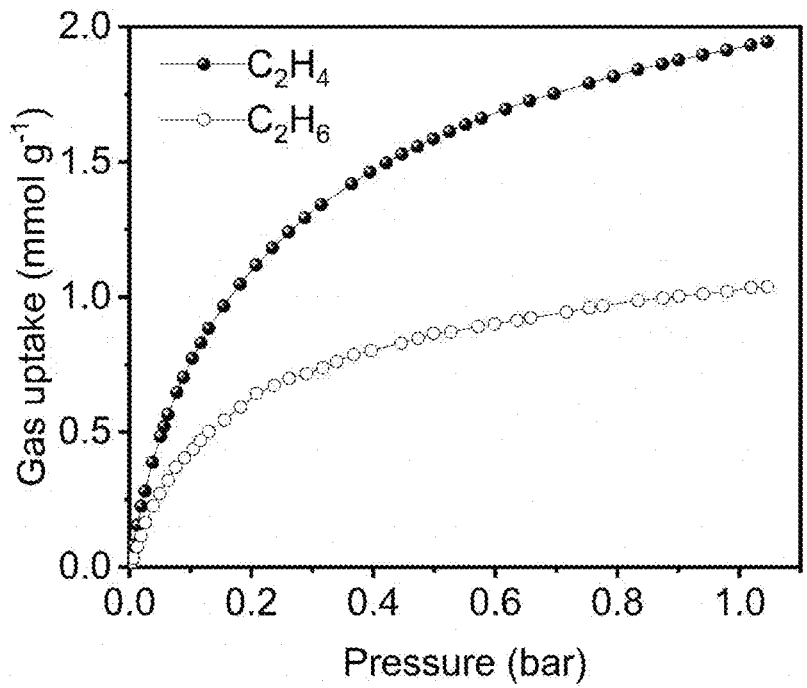
FIG. 3 shows the adsorption isotherms of $C_2H_4$ and $C_2H_6$ at 298 K on the ultramicroporous metal-organic framework Zn-Atz-$PO_4$ synthesized in exampled 1.
Figure 4:
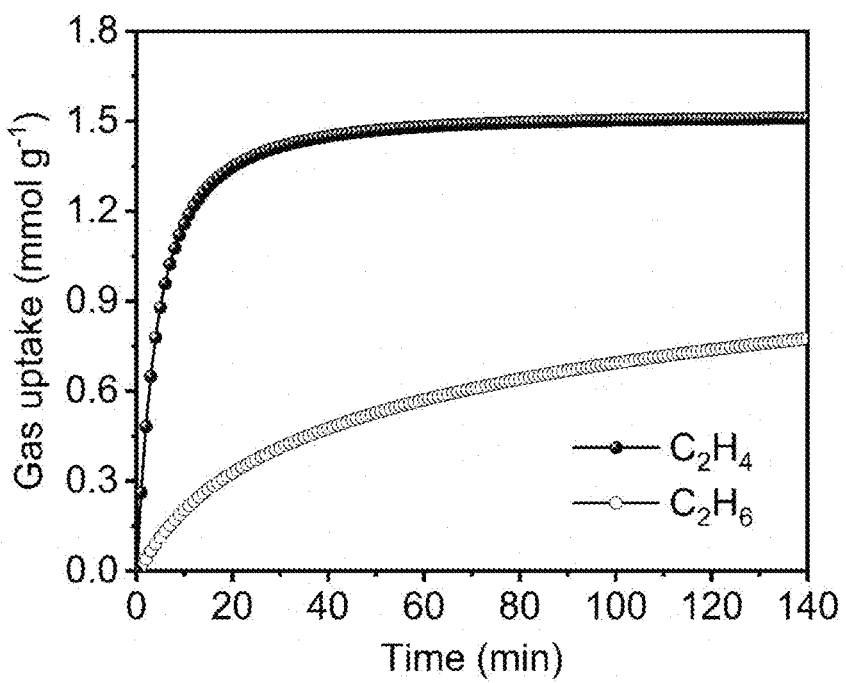
FIG. 4 shows the time-dependent adsorption curves of $C_2H_4$ and $C_2H_6$ at 298 K and 0.4 bar on the ultramicroporous metal-organic framework Zn-Atz-$PO_4$ synthesized in exampled 1.
Figure 5:
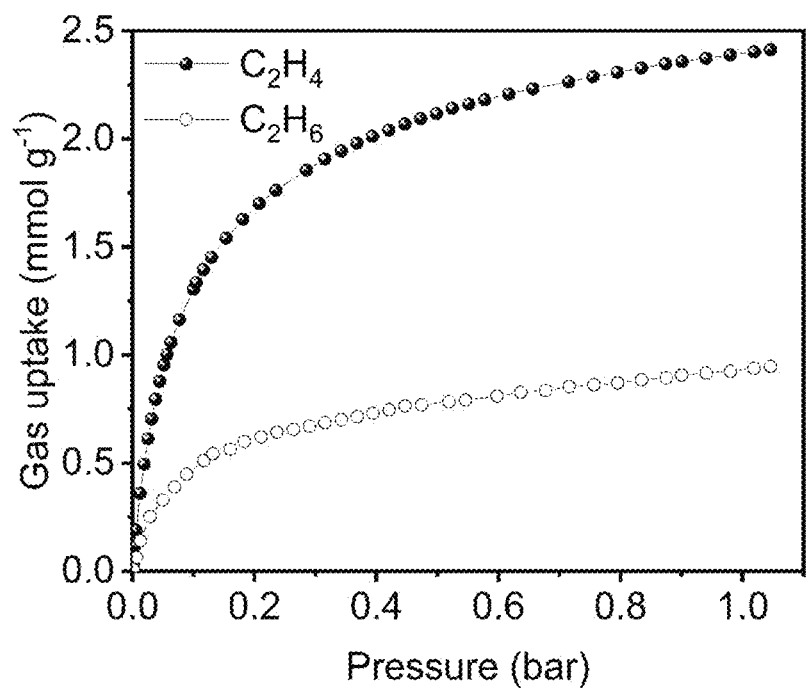
FIG. 5 shows the adsorption isotherms of $C_2H_4$ and $C_2H_6$ at 273 K on the ultramicroporous metal-organic framework Zn-Atz-$PO_4$ synthesized in exampled 1.
Figure 6:
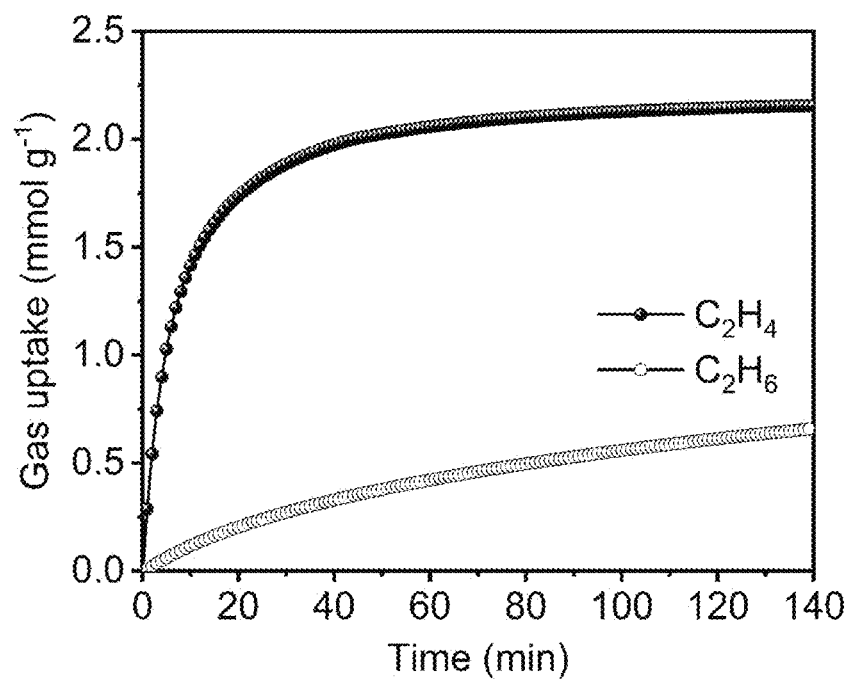
FIG. 6 shows the time-dependent adsorption curves of $C_2H_4$ and $C_2H_6$ at 273 K and 0.4 bar on the ultramicroporous metal-organic framework Zn-Atz-$PO_4$ synthesized in exampled 1.

The method described in the literature (Angewandte Chemie, 2012, 124(8): 1862-1865.) was used to synthesize the ultra-microporous metal organic frame material Zn-Atz-$PO_4$ by using phosphoric acid, $Zn(OH)_2 \cdot 2ZnCO_3$ and 3-amino-1,2,4-triazole as raw materials. The powder X-ray diffraction pattern of Zn-Atz-$PO_4$ is shown in FIG. 1, which agrees well with the literature report. The narrowest part of the material pore size is 3.8 Å. The thermal gravimetric analysis curve of Zn-Atz-$PO_4$ is presented in FIG. 2, which suggests a high thermal decomposition temperature of nearly 420° C.

The adsorption isotherms and time-dependent adsorption profiles of $C_2H_4$ and $C_2H_6$ on Zn-Atz-$PO_4$ were collected at 273 K and 298 K as can be seen from FIG. 3-6. The results indicate that the metal-organic framework simultaneously presents higher equilibrium uptake capacity and faster adsorption rate for $C_2H_4$ in contrast to $C_2H_6$. Under 273 K, the thermodynamic selectivity and kinetic selectivity ($C_2H_4$/$C_2H_6$) of Zn-Atz-$PO_4$ is calculated to be 4 and 27, respectively, leading to an excellent equilibrium-kinetics combined selectivity of 20, exceeding ITQ-55 (~6), the best material for kinetic separation of ethylene and ethane.

Figure 7:
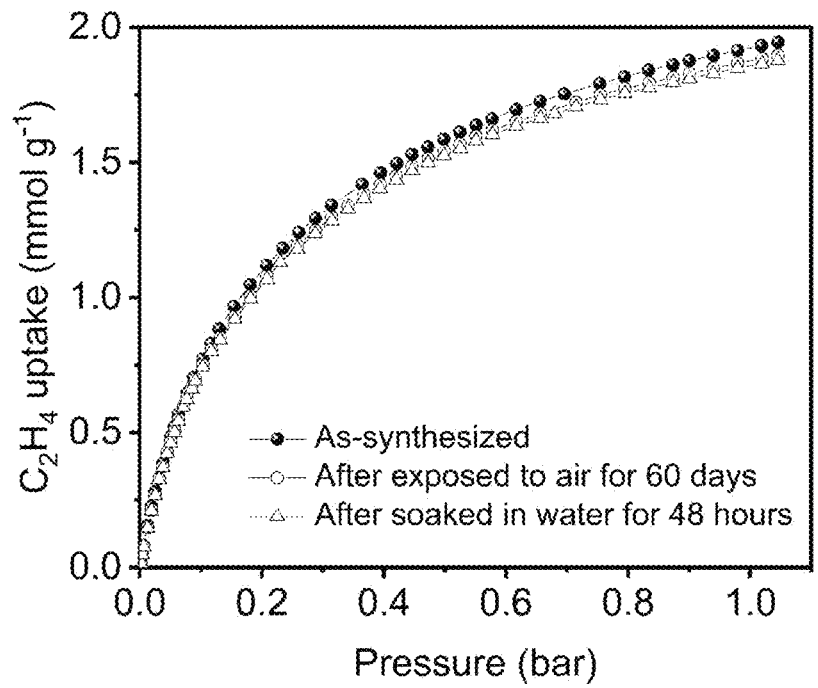
FIG. 7 shows the $C_2H_4$ adsorption isotherms at 298 K on water/air treated Zn-Atz-$PO_4$ synthesized in exampled 1.

The obtained Zn-Atz-$PO_4$ material was exposed to air (25° C., relative humidity 70%) for 60 days or soak in water for 48 hours. Then the material was analyzed by X-ray diffraction, and the adsorption isotherm of ethylene on the material at 298 K was measured again. The results were shown in FIG. 1 and FIG. 7. The results showed that the Zn-Atz-$PO_4$ material exposed to water and air environment for a long time can still maintain a complete crystal structure, and compared with the newly synthesized sample, the ethylene adsorption capacity does not decrease significantly, indicating that Zn-Atz-$PO_4$ has excellent stability.

Example 2

$CoCO_3$, $Na_3VO_4$, and 3-chloro-1H-1,2,4-triazole with a mass ratio of 1:1:4 were firstly poured into an aqueous solution comprising $H_2O$ and ethanol in volume ratio of 1:1, followed by adjusting the pH of the resulting mixture to 8.5 using hydrochloric acid. After that, the mixture was placed in an oven under 120° C. for 48 hours, then after reaction, the mixture was cooled to room temperature naturally. The precipitation was further collected by filtration and washed with methanol. Last, the product was heated at 100° C. under high vacuum for 12 hours to obtain the ultramicroporous metal-organic framework Co-Cltz-$VO_4$.

The as-synthesized ultramicroporous metal-organic framework Co-Cltz-$VO_4$ was packed into a fixed-bed sorption column with a length of 5 cm. Then, breakthrough experiment was carried out by introducing $C_2H_4/C_2H_6$ mixture (90:10, v/v) into the column under 298 K and 8 bar with a flow rate of 2 mL $min^{-1}$. The slow-diffusing $C_2H_6$ component flowed out of the column firstly, and high-purity $C_2H_6$ (99.99%) can be directly obtained from the outlet. The flow of $C_2H_4/C_2H_6$ gas mixture was turned off upon $C_2H_4$ broke through the column. After that, the column was purged with 5 mL of He, then the column pressure was reduced to less than 0.2 bar, so that $C_2H_4$ with a high purity of 95% can be released from the column and the regeneration of Co-Cltz-$VO_4$ can be achieved.

Example 3

Figure 8:
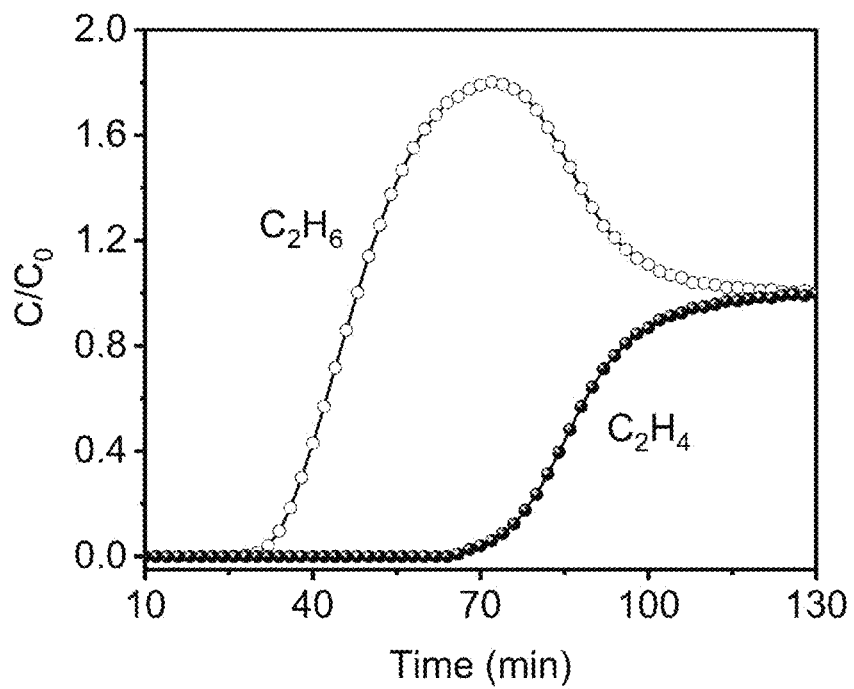
FIG. 8 shows the breakthrough curves of the ethylene/ethane mixed gas (volume ratio 50:50) obtained in example 3.
Figure 9:
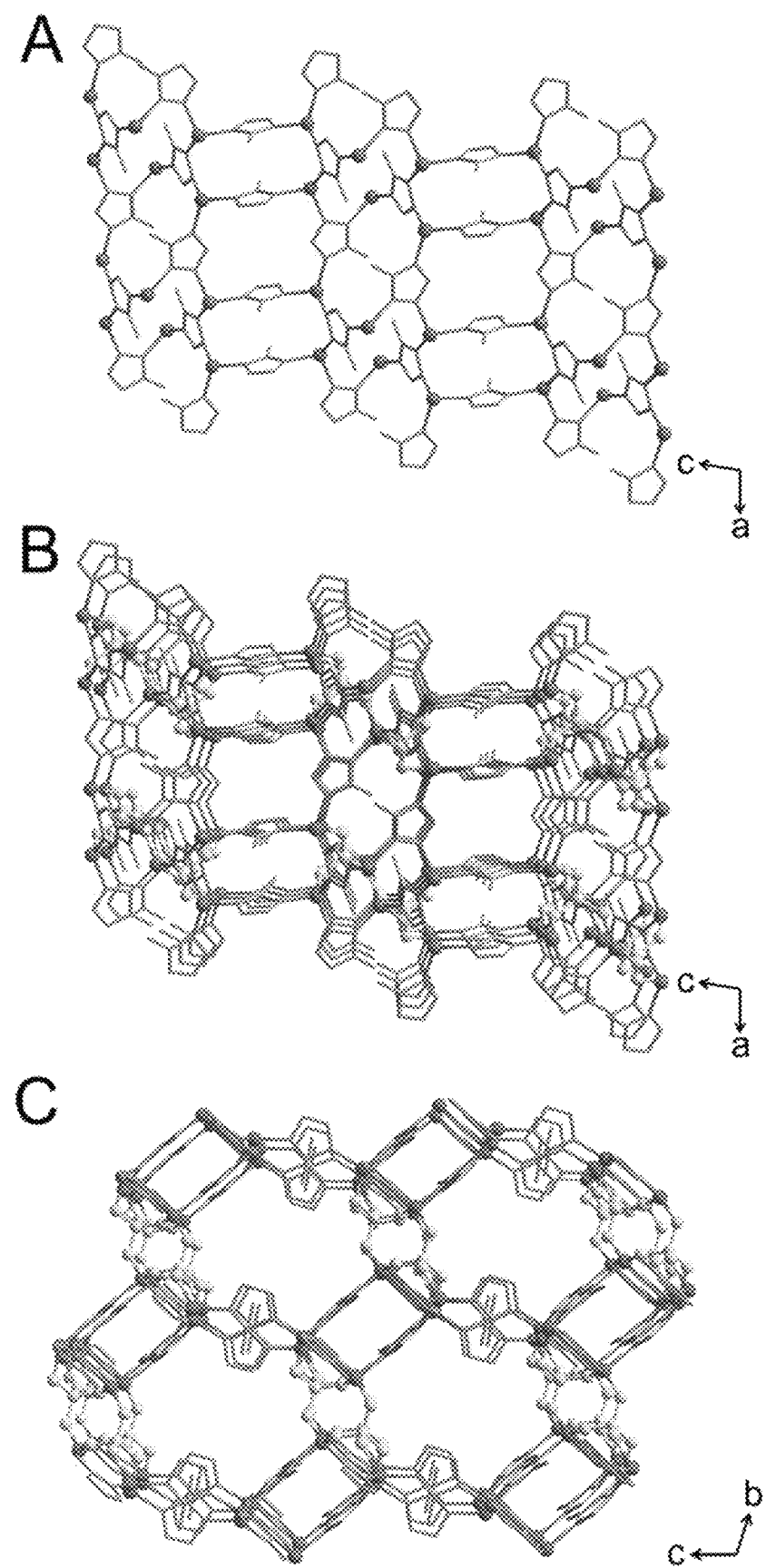
FIG. 9 shows the structure of the ultramicroporous metal-organic framework described in the present invention (wherein a and b are from two different angles).

The ultramicroporous metal-organic framework Zn-Atz-$PO_4$ synthesized in example 1 was packed into a fixed-bed sorption column with a length of 5 cm, and breakthrough experiment was then carried out under 273 K and 1 bar by introducing a flow of $C_2H_4/C_2H_6$ mixture (50:50, v/v) into the column with a rate of 0.5 mL $min^{-1}$. As can be seen from the obtained breakthrough curves presented in FIG. 8, high-purity $C_2H_6$ (99.999%) flowed out of the column quickly after 27 min, while $C_2H_4$ was continuously adsorbed by Zn-Atz-$PO_4$ until its breakthrough point of 70 min. After that, the $C_2H_4/C_2H_6$ gas flow was turned off. The column was further purged with 5 mL of high-purity $C_2H_4$ produced in exampled 2, followed by decreasing the column pressure to <0.05 bar and heating the column to 65° C., so that $C_2H_4$ with a high purity of 99% can be released from the column and the regeneration of Zn-Atz-$PO_4$ can be realized.

Example 4

After Zn-Atz-$PO_4$ was regenerated as described example 3, breakthrough experiment was again carried out on the same fixed bed by introducing a flow of $C_2H_4/C_2H_6/N_2$ mixture (90:5:5, v/v/v) into the column under 273 K and 2 bar with a rate 1.0 mL $min^{-1}$. Upon the experiment started, $N_2$ flowed out of the column immediately due to steric effect. Next, $C_2H_6$ also broke through and high-purity $C_2H_6$ (>95%) can be directly obtained from the outlet. After $C_2H_4$ penetrated the column, the $C_2H_4/C_2H_6/N_2$ flow was turned off. The column was further purged with 10 mL of high-purity $C_2H_4$ produced in example 2, and then the column pressure was reduced to <0.02 bar, so that $C_2H_4$ adsorbed in the fixed bed with a high purity of 98% can be released and the regeneration of Zn-Atz-$PO_4$ can be accomplished.

Example 5

$Zn(OH)2.2ZnCO_3$, 3-methyl-1H-1,2,4-triazole, and phosphoric acid (85% water solution) with a mass ratio of 1:4:0.35 were poured into an aqueous solution comprising $H_2O$ and of ethanol in volume ratio of 1:1, followed by adjusting the pH of the resulting mixture to 7.5 using aqueous ammonia. After that, the mixture was placed in an oven under 180° C. for 48 hours, then cooled to room temperature naturally. The precipitation was further collected by filtration and washed with methanol. Last, the product was heated at 100° C. under high vacuum for 12 hours to obtain the ultramicroporous metal-organic framework Zn-Ctz-$PO_4$.

The adsorption isotherms of $C_2H_4$ and $C_2H_6$ on the resultant Zn-Ctz-$PO_4$ were measured at 298 K. Under a pressure of 1 bar, the equilibrium uptake capacity of $C_2H_4$ can be 1.5 mmol $g^{-1}$, equivalent to three times that of $C_2H_6$ (0.5 mmol $g^{-1}$).

Example 6

$2NiCO_3.3Ni(OH)_2$, 1H-1,2,4-triazole and phosphoric acid (85% water solution) with a mass ratio of 1:4:0.35 were poured into an aqueous solution comprising $H_2O$ and ethanol in volume ratio of 1:1, followed by adjusting the pH of the resulting mixture to 7.5 using aqueous ammonia. After that, the mixture was placed in an oven under 180° C. for 72 hours, then cooled to room temperature naturally. The precipitation was further collected by filtration and washed with methanol. Last, the product was heated at 100° C. under high vacuum for 12 hours to obtain the metal-organic framework Ni-Tz-$PO_4$.

The as-synthesized Ni-Tz-$PO_4$ was packed into a fixed-bed sorption column with a length of 5 cm, and then breakthrough experiment was carried out by introducing a flow of $C_2H_4/C_2H_6$ mixture (85:15, v/v) into the column under 263 K and 10 bar with a rate of 2 mL $min^{-1}$. During this period, high-purity $C_2H_6$ (99.999%) can be directly harvested from the outlet of the column. After $C_2H_4$ broke through, the flow of $C_2H_4/C_2H_6$ mixture was turned off. The column was heated to 100° C. with the pressure reduced to less than 1 bar, so that the adsorbed $C_2H_4$ component with a purity of >93% can be released from the column. The recovery rate of $C_2H_4$ can be 75%.

Example 7

$Cu_2(OH)_2CO_3$, 3-bromo-1H-1,2,4-triazole and phosphoric acid with a mass ratio of 1:4:0.4 were poured into an aqueous solution comprising 2 mL of $H_2O$ and 2 mL of butanol, followed by adjusting the pH of the resulting mixture to 7.5 using aqueous ammonia. After that, the mixture was placed in an oven under 180° C. for 48 hours, then cooled to room temperature naturally. The precipitation was further collected by filtration and washed with methanol. Last, the product was heated at 100° C. under high vacuum for 12 hours to obtain the ultramicroporous metal-organic framework Cu-Brtz-$PO_4$.

The as-synthesized Cu-Brtz-$PO_4$ was shaped into 1~2 mm pellets by extruding, which were then packed into a fluidized-bed sorption column. Breakthrough experiment was carried out by introducing a flow of $C_2H_4/C_2H_6$ mixture (10:90, v/v) into the column under 313 K and 5 bar with a rate of 2 mL $min^{-1}$. During this period, high-purity $C_2H_6$ (99.99%) can be directly obtained from the outlet of the sorption column. After $C_2H_4$ broke through, the flow of $C_2H_4/C_2H_6$ mixture was turned off. The column was purged with 10 mL of high-purity $C_2H_4$ produced in example 2, followed by reducing the column pressure to less than 0.1 bar, so that the adsorbed $C_2H_4$ component with a purity of >95% can be released from the adsorbent.

Example 8

$Zn(OH)_2.2ZnCO_3$, 3-fluoro-1H-1,2,4-triazole and phosphoric acid (85% water solution) with a mass ratio of 1:4:0.35 were poured into an aqueous solution comprising H₂O and methanol in volume ratio of 1:1, followed by adjusting the pH of the resulting mixture to 7.5 using aqueous ammonia. After that, the mixture was placed in an oven under 180° C. for 48 hours, then cooled to room temperature naturally. The precipitation was further collected by filtration and washed with methanol. Last, the product was heated at 100° C. under high vacuum for 12 hours to obtain the ultramicroporous metal-organic framework Zn-Ftz-PO₄. The as-synthesized Zn-Ftz-PO₄ was shaped into 1~2 mm pellets by extruding, which were then packed into a moving-bed sorption column. Breakthrough experiment was conducted under 273 K and 4 bar by introducing a flow of C₂H₄/C₂H₆/CH₄ mixture (90:5:5, v/v/v) into the column with a rate of 4 mL min⁻¹. After C₂H₄ eventually penetrated the sorption column, the C₂H₄/C₂H₆/CH₄ flow was turned off. Then, high-purity C₂H₄ (>95%) can be leased from the metal-organic framework by heating the column to 100° C., and the regeneration of Zn-Ftz-PO₄ can be realized at the same time.

Example 9

Zn(OH)₂·2ZnCO₃, 3-mercapto-1,2,4-triazole and phosphoric acid (85% aqueous solution) in a mass ratio of 1:4:0.35 were added into a 1:1 volume ratio of water/methanol mixed solvent and stirred evenly in the medium, and ammonia water was added to adjust the pH of the reaction solution to 7.5, and then the mixture was placed in an oven at 180° C. for 48 hours. After the reaction, the obtained solid product was collected by suction filtration, washed with methanol several times, and the sample was activated at 100° C. in a vacuum environment for 12 hours to obtain the metal organic framework material Zn-Stz-PO₄.

The as-synthesized Zn-Stz-PO₄ was packed into a fixed-bed sorption column with a length of 5 cm, and breakthrough experiment was carried under 323 K and 2 bar by introducing a flow of C₂H₄/C₂H₆/CO₂ mixture (90:9:1, v/v/v) into the column with a rate of 1 mL min⁻¹. During this period, high-purity C₂H₆ (99.9%) can be continuously harvested from the outlet of the column. After C₂H₄ eventually broke through, the flow of C₂H₄/C₂H₆/CO₂ mixture was turned off. The column was purged with 5 mL of high-purity C₂H₄ produced in example 2, followed by reducing the column pressure to less than 0.05 bar, so that the adsorbed C₂H₄ with a purity of (97%) can be released from the bed, and the regeneration of Zn-Stz-PO₄ can be realized.

Furthermore, the foregoing descriptions of the embodiments according to the present invention are provided for illustration only, not for the purpose of limiting the invention as defined by the appended claims and their equivalents. Although only the selected embodiments have been chosen to illustrate the present invention, the all involved change or modification without departing from the scope of the invention as defined in the appended claims are covered in this invention.

The invention claimed is:

1. A method for adsorptive separation of ethylene and ethane using an ultramicroporous metal-organic framework material as an adsorbent, comprising the following steps: contacting a C₂H₄/C₂H₆ mixture with the ultramicroporous metal-organic framework material; adsorbing C₂H₄ from the mixture to separate C₂H₄ from C₂H₆;
wherein the ultramicroporous metal-organic framework material has a formula of [M₃L₃A]∞; wherein M is a metal cation, L is an organic linker, and A is an oxygen-containing inorganic anion, in which the organic linker is selected from 1,2,4-triazole and its derivatives having a formula of:

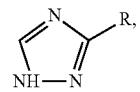

wherein R is one of H, CH₃, NH₂, SH, F, Cl, and Br;
wherein the metal cation is one of Cu²⁺, Zn²⁺, Co²⁺, and Ni²⁺; and
wherein the oxygen-containing inorganic anion is one of PO₄³⁻ and VO₄³⁻.

2. The adsorptive separation method according to claim 1, wherein the ultramicroporous metal-organic framework material has one-directional straight pore channels with a periodically expanded and contracted cross-section, wherein the minimum pore size is in the range of 3.0~4.2 A, and the pore surface is decorated by the oxygen-containing inorganic anion.

3. The adsorptive separation method according to claim 1, wherein the ultramicroporous metal-organic framework material is made by the following method, wherein precursors of the metal cation, the organic linker, and the oxygen-containing inorganic anion are mixed with 0.1! water/alcohol solution in an alkaline condition, then heated under certain temperatures;
wherein the precursors of the organic linker and the metal cation are in a mole ratio of 1:1~50:1;
wherein the precursors of the organic linker and the oxygen-containing inorganic anion are in a mole ratio of 1:1 ~ 50:1; and
wherein the certain temperatures are in the range of 65~210° C.

4. The adsorptive separation method according to claim 1, wherein the oxygen-containing inorganic anion is PO₄³⁻, the metal cation is Zn²⁺, and the organic linker is 3-methyl-1,2,4-triazole.

5. The adsorptive separation method according to claim 1, wherein the oxygen-containing inorganic anion is PO₄³⁻, the metal cation is Zn²⁺, and the organic linker is 3-amino-1,2,4-triazole.

6. The adsorptive separation method according to claim 1, wherein the volume ratio of C₂H₄ and C₂H₆ is in the range of 1:99~99:1.

7. The adsorptive separation method according to claim 1, wherein the C₂H₄/C₂H₆ mixture is_contacting with the ultramicroporous metal-organic framework material by any one of fixed-bed adsorptive separation, fluidized-bed adsorptive adsorption, and moving-bed adsorptive separation.

8. The adsorptive separation method according to claim 1, wherein the separation of ethylene and ethane from each other is implemented by a fixed-bed adsorptive separation, which comprises the following steps:
(1) under a set adsorption temperature and a set pressure, feeding the ethylene and ethane mixture into a fixed bed adsorption column filled with the ultramicroporous metal organic framework material at a set flow rate, such that the ethane preferentially penetrates the bed, and ethane gas is obtained directly from an outlet of the adsorption column;
(2) enriching the bed with ethylene; and
(3) after the ethylene penetrates the bed, obtaining ethylene gas through desorption.

9. The adsorptive separation method according to claim 8, wherein the set adsorption temperature is in the range of −50~100° C., and the set pressure is in the range of 0~10 bar.

10. The adsorptive separation method according to claim 8, wherein the set adsorption temperature is in the range of 25~150° C., and the set pressure is in the range of 0~1 bar.

* * * * *